United States Patent
Altmann et al.

(10) Patent No.: US 8,320,711 B2
(45) Date of Patent: Nov. 27, 2012

(54) ANATOMICAL MODELING FROM A 3-D IMAGE AND A SURFACE MAPPING

(75) Inventors: Andres Claudio Altmann, Haifa (IL); Assaf Govari, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1360 days.

(21) Appl. No.: 11/950,850

(22) Filed: Dec. 5, 2007

(65) Prior Publication Data

US 2009/0148012 A1    Jun. 11, 2009

(51) Int. Cl.
*A61B 5/00* (2006.01)

(52) U.S. Cl. ........ 382/294; 382/128; 382/154; 382/276; 382/291; 382/295; 600/407; 600/434; 600/435; 600/437

(58) Field of Classification Search ............... 382/128, 382/276, 285, 291, 294, 295, 154; 600/407, 600/434, 435, 437
See application file for complete search history.

(56) References Cited

U.S. PATENT DOCUMENTS

| | | | |
|---|---|---|---|
| 4,751,643 A | 6/1988 | Lorensen et al. | |
| 5,187,658 A | 2/1993 | Cline et al. | |
| 5,568,384 A | 10/1996 | Robb et al. | |
| 5,738,096 A | 4/1998 | Ben-Haim | |
| 5,903,664 A | 5/1999 | Hartley et al. | |
| 6,106,446 A | 8/2000 | Kelly et al. | |
| 6,226,542 B1 | 5/2001 | Reisfeld | |
| 6,556,695 B1 | 4/2003 | Packer et al. | |
| 6,716,166 B2 | 4/2004 | Govari | |
| 6,773,402 B2 | 8/2004 | Govari et al. | |
| 7,517,318 B2 * | 4/2009 | Altmann et al. | 600/459 |
| 7,876,938 B2 * | 1/2011 | Huang et al. | 382/128 |
| 7,918,793 B2 * | 4/2011 | Altmann et al. | 600/437 |
| 2002/0049375 A1 | 4/2002 | Strommer et al. | |
| 2003/0038802 A1 * | 2/2003 | Johnson et al. | 345/420 |
| 2006/0241434 A1 * | 10/2006 | Shimazaki | 600/437 |
| 2006/0241445 A1 * | 10/2006 | Altmann et al. | 600/443 |
| 2006/0253024 A1 * | 11/2006 | Altmann et al. | 600/437 |
| 2007/0049817 A1 | 3/2007 | Preiss et al. | |
| 2007/0078325 A1 * | 4/2007 | Fuimaono et al. | 600/407 |
| 2007/0081712 A1 * | 4/2007 | Huang et al. | 382/128 |
| 2007/0100226 A1 * | 5/2007 | Yankelevitz et al. | 600/407 |
| 2007/0106146 A1 * | 5/2007 | Altmann et al. | 600/407 |
| 2007/0167706 A1 * | 7/2007 | Boese et al. | 600/407 |

(Continued)

FOREIGN PATENT DOCUMENTS

EP    1 717 759 A1    11/2006

(Continued)

OTHER PUBLICATIONS

Canny, John A Computational Approach to Edge Detection, IEEE Transactions on Pattern Analysis and Machine Intelligence, vol. PAMI-8, No. 6, 679-698, Nov. 1986.

(Continued)

*Primary Examiner* — Michael Logie
(74) *Attorney, Agent, or Firm* — Louis J. Capezzuto

(57) ABSTRACT

A method of medical imaging includes creating an anatomical map of an inner wall of a cavity in a body of a subject by inserting a probe into the body and collecting data using the probe. A three dimensional (3-D) contour is delineated in a 3-D image of the cavity based on the map.

26 Claims, 7 Drawing Sheets

U.S. PATENT DOCUMENTS

2009/0275830 A1* 11/2009 Falco et al. .................. 600/437

FOREIGN PATENT DOCUMENTS

| JP | 2002315754 A | * | 10/2002 |
| WO | WO 99/55233 A1 | | 11/1999 |
| WO | WO 00/07501 A1 | | 2/2000 |

OTHER PUBLICATIONS

McInerney, Tim et al. Deformable Models in Medical Image Analysis: A Survey, Medical Image Analysis, 1(2):91-108, 1996.

Neubauer, Andre et al. Analysis of Four-Dimensional Cardiac Data Sets Using Skeleton-Based Segmentation, Journal of WSCG, vol. 11, No. 1., Feb. 3-7, 2003.

Partial European Search Report EPO8 25 3877 dated Mar. 19, 2009.

Abolmaesumi, P. "An Interacting Multiple Model Probabilistic Data Association Filter for Cavity Boundary Extraction From Ultrasound Images", IEEE Transactions on Medical Imaging, vol. 23, No. 6, pp. 772-784, Jun. 2004.

Noble, J. Alison, "Ultrasound Image Segmentation: A Survey", IEEE Transactions on Medical Imaging, vol. 25, No. 8, pp. 987-1010, Aug. 2006.

Wolf, I. et al. "Ropes: A Semiautomated Segmentation Method for Accelerated Analysis of Three-Dimensional Echocardiographic Data", IEEE Transactions on Medical Imaging, vol. 21, No. 9, pp. 1091-1104, Sep. 2002.

Zaim, A. "Automatic Segmentation of the Prostate From Ultrasound Data Using Feature-Based Self Organizing Map", Image Analysis, Springer-Verlag, Berlin/Heidelberg, vol. 3540, pp. 1259-1265, Jun. 2005.

* cited by examiner

ANATOMICAL MODELING FROM A 3-D IMAGE AND A SURFACE MAPPING

FIELD OF THE INVENTION

The present invention relates generally to medical imaging systems, and particularly to methods and systems for constructing three-dimensional views of internal organs.

BACKGROUND OF THE INVENTION

Three-dimensional (3-D) images of internal organs are useful in many catheter-based diagnostic and therapeutic applications, and real-time imaging is widely used during surgical procedures. Ultrasound imaging is a relatively convenient mode of real-time imaging, though the resolution of real-time ultrasound images is generally not as good as the resolution obtained from other imaging modalities, such as computerized tomography (CT) and magnetic resonance imaging (MRI).

U.S. Pat. No. 6,106,466 to Sheehan, et al., whose disclosure is incorporated herein by reference, describes a method for generating a 3-D model of a heart from 2-D ultrasound images. Anatomical locations are manually identified in the 2-D images. A 3-D mesh serves as an archetypal heart shape, which is aligned with the anatomical locations so as to delineate the 3-D model.

Methods for segmenting 3-D structures by tissue type are known in the art. U.S. Pat. No. 4,751,643 to Lorensen, et al., whose disclosure is incorporated herein by reference, describes a method for determining how slices of a structure are connected across 2-D images. An operator specifies a threshold of intensity that identifies a tissue type to be displayed. The operator also selects an initial voxel, or seed, identifying the location of the structure. U.S. Pat. No. 5,187,658 to Cline, et al., whose disclosure is incorporated herein by reference, describes a method for segmenting internal structures by constructing a statistical probability distribution based on relative intensities of tissues as they appear in a 3-D image.

U.S. Pat. No. 5,903,664 to Hartley, et al., whose disclosure is incorporated herein by reference, describes a method for segmentation based on selecting a seed point within a region of interest (ROI), such as the left ventricle. The seed point is expanded to include points within the ROI that have the same classification as the seed point, based on a threshold value.

U.S. Patent Application Publication 2006/0253024 to Altmann, et al., whose disclosure is incorporated herein by reference, describes a method in which an operator marks contours-of-interest in one or more ultrasound images. A 3D model of the anatomical structure is constructed based on the contours of interest and on measured location and orientation coordinates of the ultrasonic sensor.

U.S. Patent Application Publication 2007/0049817 to Preiss, et al., whose disclosure is incorporated herein by reference, describes a method for registering 3-D images with cardiac maps that comprise discrete points. The registration is performed by identifying sites of functional or physiological information, such as scar tissue, while acquiring points in the cardiac map. The sites are manually identified in the 3-D image, and the map and the 3-D image are registered according to the identified sites common to the two.

U.S. Patent Application Publication 2007/0106146 to Altmann, et al., whose disclosure is incorporated herein by reference, discloses a method and system for synchronizing the acquisition of an electro-anatomical map and a 3-D ultrasound image and subsequently displaying overlaid, cyclical motion of the two.

U.S. Patent Application Publication 2002/0049375 to Strommer describes a method for displaying an image sequence of a cyclically moving organ. An organ timing signal is detected, and a plurality of two-dimensional images of the organ are acquired from different locations and orientations using an image detector. Each of the two-dimensional images is associated with its corresponding image detector location and orientation and with a reading of the organ timing signal. The two-dimensional images are grouped according to cycle points in the organ motion cycle, and each group is used in reconstructing a three-dimensional image associated with the respective cycle point.

Methods for 3-D mapping of a heart using a position-sensing catheter are well known in the art. For example, U.S. Pat. No. 5,738,096 to Ben-Haim, whose disclosure is incorporated herein by reference, describes a position-sensing probe brought into contact with multiple points in the body so as to generate an anatomical map. Physiological properties, including electrical activity on the surface of the heart, may also be acquired by the catheter. (Generation of such an electro-anatomical map may be performed with a CARTO™ navigation and mapping system, manufactured and sold by Biosense Webster, Inc., of Diamond Bar, Calif.)

U.S. Pat. No. 6,226,542 to Reisfeld, whose disclosure is incorporated herein by reference, describes a method for generating a 3-D model based on a cardiac map. An arbitrary, closed 3D curved surface is roughly adjusted to a shape which resembles a reconstruction of the points of the map. Thereafter, a flexible matching stage is performed to bring the closed surface to accurately resemble the shape of the actual volume being reconstructed.

Some medical imaging systems apply methods for registering multiple 3-D models. For example, U.S. Pat. No. 5,568,384 to Robb, et al., whose disclosure is incorporated herein by reference, describes a method for synthesizing multiple 3-D image sets into a single composite image. A transformation of one image is performed to align it with a second image. U.S. Pat. No. 6,556,695, issued to Packer, et al., whose disclosure is incorporated herein by reference, suggests that a magnetic resonance image can be acquired, and then registered with a subsequently acquired electrical activation map or ultrasound image.

An ultrasound catheter may be used for imaging of the endocardium (i.e., the inner surfaces of the heart). For example, U.S. Pat. No. 6,716,166 to Govari and U.S. Pat. No. 6,773,402 to Govari, et al., whose disclosures are incorporated herein by reference, describe systems for reconstructing body cavities from two dimensional (2-D) images obtained with an ultrasound catheter. The catheter may also comprise position sensors, which determine coordinates of the catheter within a body cavity. Acoustic transducers in the catheter emit ultrasonic waves that are reflected from a surface of the cavity. The distance from each of the transducers to the surface is determined, and the distance measurements and the catheter position are combined so as to reconstruct the three-dimensional (3-D) shape of the cavity.

A report by McInerney and Terzopoulos, appearing in "Deformable Models in Medical Image Analysis: A Survey," *Medical Image Analysis* (1:2), June 1996, pages 91-108, which is incorporated herein by reference, describes a computer-assisted medical image analysis technique for segmenting, matching, and tracking anatomical structures by exploiting (bottom-up) constraints derived from the image data together with (top-down) a priori knowledge about the location, size, and shape of these structures.

Another analysis technique is described by Neubauer and Wegenkittl in "Analysis of Four-Dimensional Cardiac Data Sets Using Skeleton-Based Segmentation," the 11$^{th}$ International Conference in Central Europe on Computer Graphics, Visualization and Computer Vision, University of West Bohemia, Plzen, Czech Republic, February 2003, which is incorporated herein by reference. The authors describe a computer-aided method for segmenting parts of the heart from a sequence of cardiac CT (Computerized Tomography) images, taken at a number of time points over the cardiac cycle.

SUMMARY OF THE INVENTION

Embodiments of the present invention provide systems, means, and methods for modeling a three-dimensional (3-D) anatomical structure, including automated segmentation of a 3-D image along a 3-D segmentation contour and enhancement of a 3-D map based on the segmentation contour. In some embodiments of the present invention, an anatomical map of a target structure, such as an inner surface of a heart chamber, is acquired with a position-sensing probe. Alternatively or additionally, the anatomical map may be assembled from user input delineating the target structure. Based on the anatomical map, a 3-D segmentation contour in a 3-D ultrasound image is determined. A specific region of the heart delineated by the segmentation contour may then be displayed based on a user input.

In some embodiments, a position sensing ultrasound catheter may be used in acquiring both the anatomical map data and the ultrasound image. Acquisition of map data and of ultrasound images may be gated at a single point of time in the cardiac cycle or may be gated at multiple, synchronized points in the cardiac cycle, so that the specific segmented region is displayed with movement corresponding to the cardiac cycle.

In further embodiments, a transformation of points from the segmentation contour provides additional data that is incorporated into the anatomical map. Acquisition of further map data may also be performed incrementally, such that the quality of displayed images is incrementally improved.

There is therefore provided, in accordance with an embodiment of the present invention, a method of medical imaging including:

creating an anatomical map of an inner wall of a cavity in a body of a subject, such as a chamber of the heart, by inserting a probe into the body and collecting data using the probe;

creating a three dimensional (3-D) image of the cavity; and delineating a 3-D contour in the 3-D image based on the map.

In a disclosed embodiment, delineating the contour includes determining a seed point based on the anatomical map. Delineating the contour may include identifying a point on the contour located between the seed point and the cavity.

In some embodiments, creating the anatomical map includes inserting the probe into the cavity and bringing the probe into contact with the inner location at multiple locations. The anatomical map includes a plurality of first points, each associated with a respective measurement of a physiological parameter made by the probe in contact with the inner wall, and the method may include adding to the anatomical map a plurality of second points based on the contour, and generating a display of the anatomical map showing a distribution of the physiological parameter over the first and second points. Typically, the physiological parameter is selected from a group of parameters consisting of cardiac electrical activity, a tissue characteristic, a temperature, and a blood flow.

In some embodiments, creating the 3-D image includes creating a 3-D ultrasound image by capturing multiple two-dimensional (2-D) ultrasound images using an ultrasonic transducer in the probe, and combining the 2-D ultrasound images to generate the 3-D image. Creating the anatomical map may include delineating respective 2-D contours in a plurality of the 2-D ultrasound images, and combining the 2-D contours to produce the anatomical map.

Additionally or alternatively, creating the 3-D ultrasound image includes determining first coordinates of pixels of the 3-D ultrasound image in a given 3-D coordinate space, and bringing the probe into contact with the inner wall of the cavity includes measuring second coordinates in the given 3-D coordinate space of one or more locations on the inner wall. In one embodiment, the anatomical map is created using a first probe, and the 3-D ultrasound image is captured using a second probe including an ultrasonic transducer, wherein the first and second probes include respective first and second position sensors, and wherein the method includes coupling the position sensors to sense generated fields and calculating positions of the first and second probes responsively to the sensed fields. In a disclosed embodiment, the probe includes an ultrasonic transducer and a position sensor, and is used both to create the anatomical map and to capture the 3-D ultrasound image.

In one embodiment, the method includes synchronizing a timing of capturing the ultrasound image and creating the anatomical map relative to a synchronizing signal selected from a group of signals consisting of an electrocardiogram (ECG) signal, an internally-generated synchronization signal and an externally-supplied synchronization signal. Typically, the timing is synchronized to multiple timing points in a cardiac cycle, and the method includes generating a display of one or more of the anatomical map, the ultrasound image, and the contour as a moving image.

Alternatively, capturing the 3-D image includes scanning the anatomical structure using an extracorporeal ultrasound probe.

In a disclosed embodiment, the method includes generating a display of the contour showing a distribution over the contour of data from at least one imaging modality selected from a group of modalities consisting of ultrasound imaging, Magnetic Resonance Imaging (MRI), Computerized Tomography (CT), and x-ray imaging.

In another embodiment, the method includes identifying a volume bounded by the contour and generating a display showing a distribution within the volume of voxels from a 3-D imaging modality.

There is also provided, in accordance with an embodiment of the present invention, a method of medical imaging, including:

inserting a probe into a body, the probe including a sensor for measuring a physiological parameter;

bringing the probe into contact with a plurality of first points on a surface of an organ in the body so as to measure the physiological parameter at each of the first points;

creating an anatomical map of the organ including the plurality of first points and representing a distribution of the physiological parameter over the surface of the organ;

receiving a three-dimensional (3-D) image of the organ;

determining a contour included in the 3-D image; and adding a plurality of second points not included among the first points to the anatomical map based on the contour.

Typically, adding the second points includes applying a transformation so as to register the contour with the anatomical map.

In some embodiments, generating a display of the anatomical map responsively to adding the plurality of second points to the anatomical map, wherein the display includes the first and second points and shows the distribution of the physiological parameter over the surface of the organ. The method may include, responsively to generating the display, bringing the probe into contact with a plurality of supplemental points on the surface of the organ so as to measure the physiological parameter at each of the supplemental points, adding the supplemental points to the anatomical map, and regenerating the display of the anatomical map including the third points.

There is additionally provided, in accordance with an embodiment of the present invention, a method of medical imaging including:

capturing a 3-D image of an anatomical structure;
determining a contour included in the 3-D image;
identifying a volume in the 3-D coordinate space bounded by the contour;
generating a picture showing voxels from a 3-D imaging modality within the volume.

In one embodiment, showing the voxels includes generating a semi-transparent visualization of one or more of the voxels. Alternatively or additionally, generating the picture includes showing a thickness of a wall of an organ that is bounded by the contour.

There is further provided, in accordance with an embodiment of the present invention, a system for medical imaging, including:

at least one probe, which is configured to be inserted into a cavity in a body of a subject and to collect data for use in creating an anatomical map of an inner wall of the cavity; and a processor, which is configured to generate a three-dimensional (3-D) image of the cavity and to delineate a 3-D contour in the image based on the map.

The system typically includes a display configured to show the picture.

In some embodiments, the system includes one or more radiators, coupled to generate fields in a vicinity of the first and second probes, and at least one position sensor, which is associated with the at least one probe and is coupled to transmit signals responsively to the generated fields, wherein the processor is configured to determine coordinates of the at least one probe responsively to the signals. In one embodiment, the processor is coupled to calculate first coordinates of the at least one position sensor in a given three-dimensional coordinate space responsively to the sensed fields and to determine, based on the first coordinates and second coordinates of pixels of the 3-D image in the given three-dimensional coordinate space, and to determine third coordinates in the given three-dimensional coordinate space of one or more locations on the inner wall.

In a disclosed embodiment, the anatomical structure includes a heart, and the at least one probe includes at least one catheter, which is inserted into the chamber so as to acquire the 3-D image and the coordinates of the anatomical map.

There is moreover provided, in accordance with an embodiment of the present invention, a system for medical imaging, including:

a probe configured to be inserted into a body, to be brought into contact with a plurality of first points on a surface of an organ in the body so as to measure a physiological parameter at each of the first points; and a processor configured to create an anatomical map of the organ including the plurality of first points and representing a distribution of the physiological parameter over the surface of the organ, to receive a three-dimensional (3-D) image of the organ, to determine a contour included in the 3-D image, and to add a plurality of second points not included among the first points to the anatomical map based on the contour.

There is furthermore provided, in accordance with an embodiment of the present invention, a system for medical imaging including:

a probe, which is configured to capture a 3-D image of an anatomical structure;

a processor configured to determine a contour in the 3-D image, to identify a volume bounded by the contour, and to generate a picture showing voxels from a 3-D imaging modality within the volume; and a display configured to display the picture.

There is also provided, in accordance with an embodiment of the present invention, a computer software product for medical imaging, the product including a computer-readable medium in which program instructions are stored, which instructions, when read by a computer, cause the computer to acquire a three-dimensional (3-D) image of a cavity in a body of a subject, to determine coordinates of an anatomical map of an inner wall of the cavity, and to delineate a 3-D contour in the 3-D image based on the map.

There is additionally provided, in accordance with an embodiment of the present invention, a computer software product for medical imaging, the product including a computer-readable medium in which program instructions are stored, which instructions, when read by a computer, cause the computer to create an anatomical map of a body organ surface including a plurality of first points and representing a distribution of a physiological parameter over the organ surface, to receive a three-dimensional (3-D) surface representation of the organ, and to add a plurality of second points not included among the first points to the anatomical map based on the 3-D surface representation.

There is further provided, in accordance with an embodiment of the present invention, a computer software product for medical imaging, the product including a computer-readable medium in which program instructions are stored, which instructions, when read by a computer, cause the computer to acquire a 3-D image of an anatomical structure, to determine a contour included in the 3-D image, to identify a volume in the 3-D coordinate space bounded by the contour, and to generate a picture showing voxels from a 3-D imaging modality within the volume.

The present invention will be more fully understood from the following detailed description of the embodiments thereof, taken together with the drawings in which:

DETAILED DESCRIPTION OF EMBODIMENTS

Figure 1:
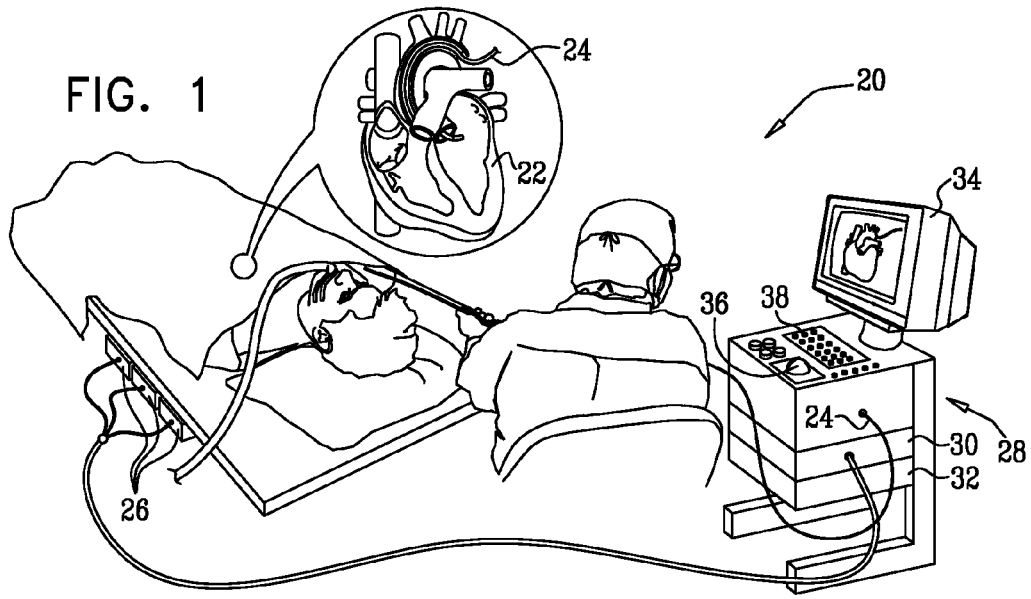
FIG. 1 is a schematic, pictorial illustration of a system for cardiac mapping and imaging, in accordance with an embodiment of the present invention.

FIG. 1 is a schematic, pictorial illustration of a system 20 for imaging and mapping a target structure, such as a heart 22 of a patient, in accordance with an embodiment of the present invention. (Hereinbelow, the term "target structure" may refer to a chamber of the heart, in whole or in part, or other body cavity, or to a particular wall, surface, blood vessel or other anatomical feature. Although the embodiments described herein refer particularly to structures in and around the heart, the principles of the present invention may similarly be applied, mutatis mutandis, in imaging of bones, muscles and other organs and anatomical structures.)

The system comprises a catheter 24, which is inserted by a physician into a chamber of the heart. Typically, catheter 24 is a position-sensing, ultrasound probe, which is configured to perform functions that include anatomical mapping and ultrasound imaging. Mapping and ultrasound imaging capabilities of catheter 24 are further described in the abovementioned U.S. Patent Publications 2006/0253024, 2007/0049817, and 2007/0106146.

A positioning sub-system of system 20 comprises a set of external radiators, such as field generating coils 26. Locations of the field generating coils are defined in a fixed coordinate space of the positioning sub-system.

Based on the fields generated by coils 26, a position sensor (FIG. 2) positioned near the distal end of catheter 24 generates position-related signals and transmits these signals to a console 28. A positioning processor 30, typically comprised in the console, calculates location coordinates of the distal end of catheter 24 from the position-related signals. In embodiments of the present invention, the distal end of the catheter is brought into contact with one or more locations on an inner surface of the heart, and the coordinates at each location are determined and stored in the console as a matrix of points. The stored matrix is referred to hereinbelow as an anatomical map.

Catheter 24 further comprises an ultrasound sensor (FIG. 2) that generates ultrasound energy and receives reflected ultrasound echoes. Based on the reflected echoes, the ultrasound sensor transmits ultrasound-related signals to an image processor 32 in console 28.

Image processor 32 typically receives the ultrasound-related signals from multiple positions and orientations of the ultrasound sensor, and processes these signals to reconstruct a 3-D ultrasound image in a 3-D space, comprising a set of voxels (i.e., 3-D pixels).

The image processor may be configured to perform other functions described in greater detail below, such as contour delineation. Using 3-D visualization techniques, the image processor also displays 3-D objects (such as delineated contours) on a display 34 of console 28. The console is interactive, enabling the physician to control displayed items using a pointing device, such as a track-ball 36, and/or to enter commands with a keyboard 38.

Typically, the functions of the positioning and image processors are implemented using a general-purpose computer, which is programmed in software to carry out the functions described herein. The software may be downloaded to the computer in electronic form, over a network, for example, or it may alternatively be supplied to the computer on tangible media, such as CD-ROM. The positioning processor and image processor may be implemented using separate computers or using a single computer, or may be integrated with other computing functions of system 20. Additionally or alternatively, at least some of the positioning and image processing functions may be performed using dedicated hardware.

Figure 2:
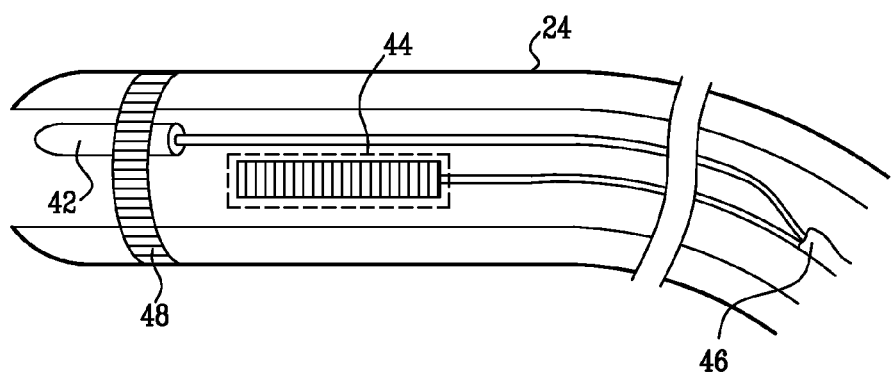
FIG. 2 is a schematic, cutaway illustration of a catheter, in accordance with an embodiment of the present invention.

FIG. 2 is a schematic, pictorial illustration that shows the distal end of catheter 24, in accordance with an embodiment of the present invention. The catheter comprises a position sensor 42 and an ultrasonic sensor 44, described hereinabove, which send respective position-related and ultrasound-related signals to console 28 by means of wires 46. Alternatively, console 28 may receive these signals by means of a wireless transmitter in catheter 24 (not shown).

In some embodiments, the distal end of the catheter comprises at least one electrode 48 for performing diagnostic and/or therapeutic functions. Electrode 48 may be used for sensing electrical potentials or cardiac activation times during generation of the anatomical map, thereby providing an electro-anatomical map. In the electro-anatomical map, location coordinates of the target structure are associated with corresponding electrical potential values.

In alternative embodiments, separate catheters may be used to acquire the ultrasound image data and the map data. The ultrasound image probe may also be extracorporeal.

Position sensor 42 is located adjacent to electrode 48 and to ultrasound sensor 44 within the distal end of catheter 24. Typically, positional and orientational offsets between position sensor 42, electrode 48, and ultrasound sensor 44 are constant and are used by positioning processor 30 to derive the coordinates of the ultrasound sensor 44 and of electrode 48. In some embodiments, the offsets are pre-calibrated and stored in positioning processor 30. Alternatively, the offsets may be stored in a memory device coupled to catheter 24.

In general, both the ultrasound images and the position measurements are synchronized with the cardiac cycle by gating data acquisition relative to a body-surface electrocardiogram (ECG) signal or intra-cardiac electrogram. Because features of the heart change their shape and position during the heart's periodic contraction and relaxation, the entire imaging process is often performed at a single trigger, or timing point, with respect to this period. Alternatively, data acquisition may be gated at multiple timing points in the cardiac cycle, so that a moving image may be displayed. In some embodiments, additional parameters that may be measured by the ultrasound sensor, such as various tissue characteristics (e.g., density or smoothness), temperature and blood flow, are also synchronized to the ECG signal.

Figure 3:
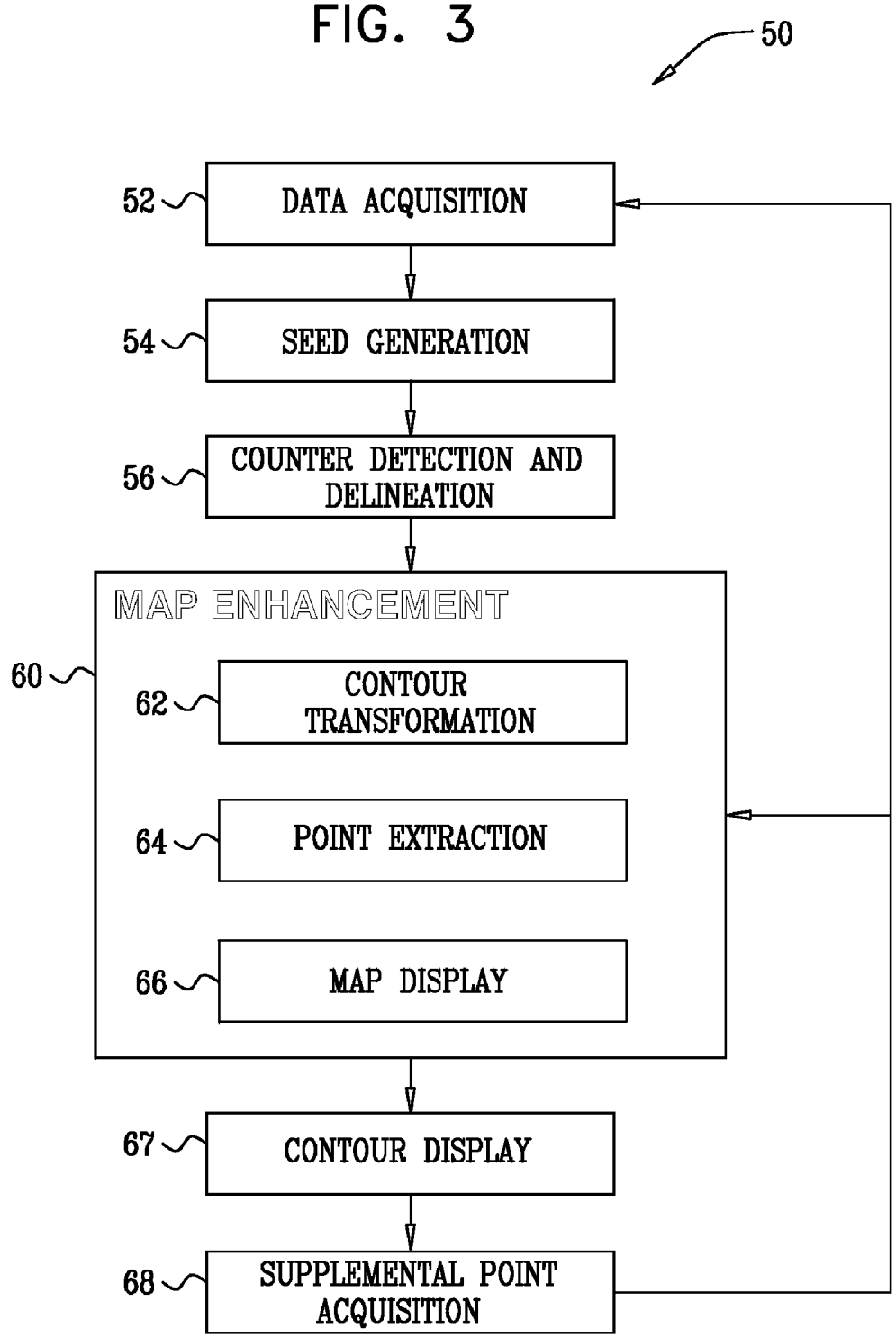
FIG. 3 is a flow chart that schematically illustrates a method for cardiac mapping and imaging, in accordance with an embodiment of the present invention.

FIG. 3 is a flow chart that schematically illustrates a process 50 for mapping and imaging of a target structure, in accordance with an embodiment of the present invention.

At a data acquisition step 52, the physician manipulates catheter 24 to acquire ultrasound image data and anatomical map data of a target structure. The ultrasound image comprises features corresponding to at least three anatomical structures, these being: first, an internal volume, within which catheter 24 is positioned, such as a chamber of a heart, a blood vessel, or a valve; second, a wall, typically having distinct inner and outer surfaces, wherein the inner surface bounds the internal volume; and third, an external volume, which corresponds to additional anatomical structures, such as a second heart chamber or body organ. The anatomical map data may be acquired by contact mapping, such as electro-anatomical mapping, in which the catheter is brought into contact with multiple points on the inner surface of the wall. Alternatively or additionally, the anatomical data may be delineated by a user of system 20, as illustrated below in FIGS. 4B-4D.

As described above, acquisition of the ultrasound image data and the anatomical map data is synchronized to a single timing point in the cardiac cycle, or to multiple timing points.

At a seed generation step 54, the image processor automatically generates from the anatomical map one or more seed points. A seed point may be a particular point comprised in the map, or may be determined by interpolation and/or extrapolation from several measured points. In one embodiment, a surface may be generated by a polynomial least-squares fit of points in the anatomical map, and a single seed point is determined as a midpoint on of the surface. Alternatively, the seed point may be chosen by a user of system 20.

Next, at a contour detection step 56, a contour in the ultrasound image is detected and delineated based on the seed point. In an exemplary embodiment, the contour is a 3-D surface corresponding to a feature that segments the image between the internal and the external sections. Typically, the contour corresponds to the inner surface of a wall bounding the internal section.

Figure 4A:
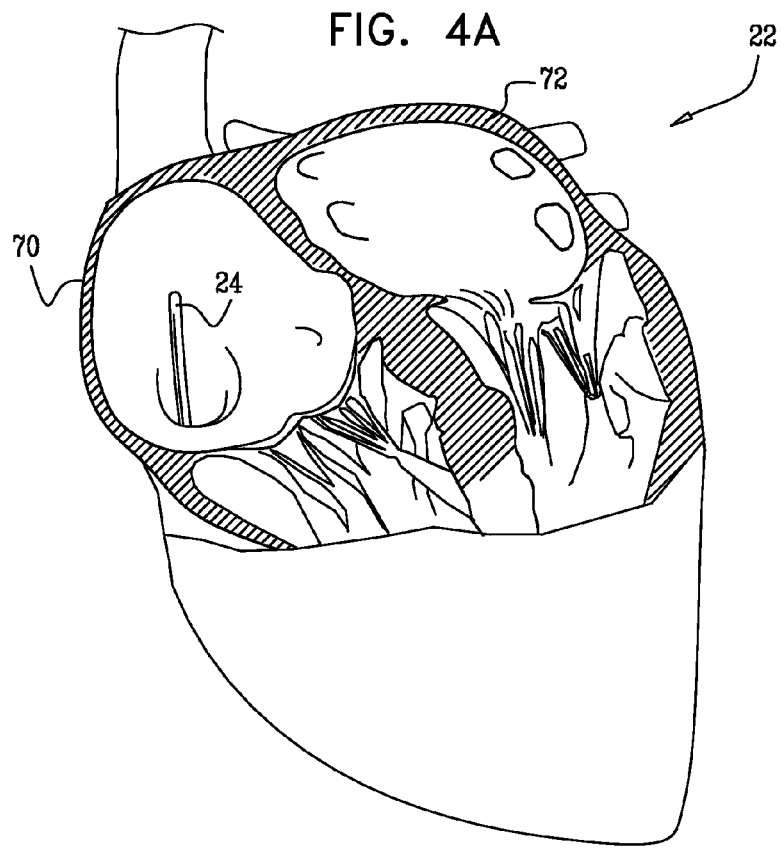
FIGS. 4A-4F, 5A-5B, 6A-6C, 7 and 8A-8B are images that visually demonstrate a method for cardiac mapping and imaging, in accordance with an embodiment of the present invention.
Figure 4B:
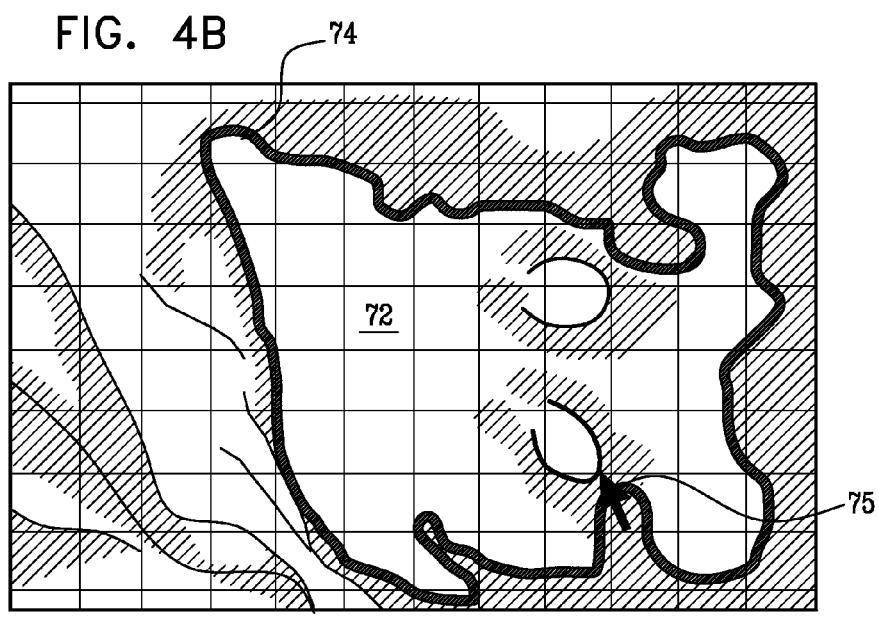
Figure 4C:
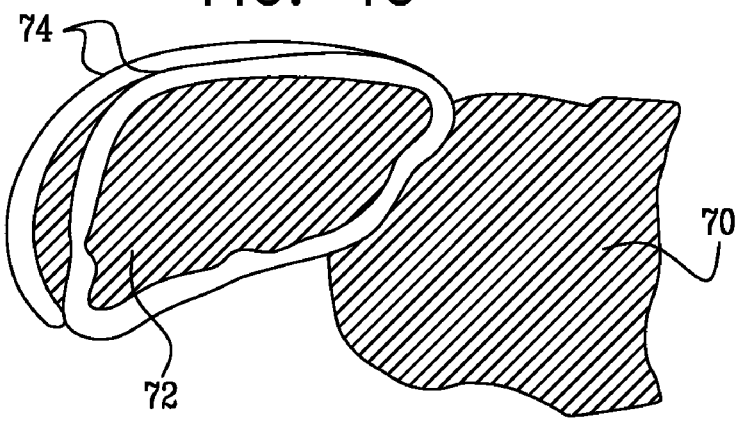
Figure 4D:
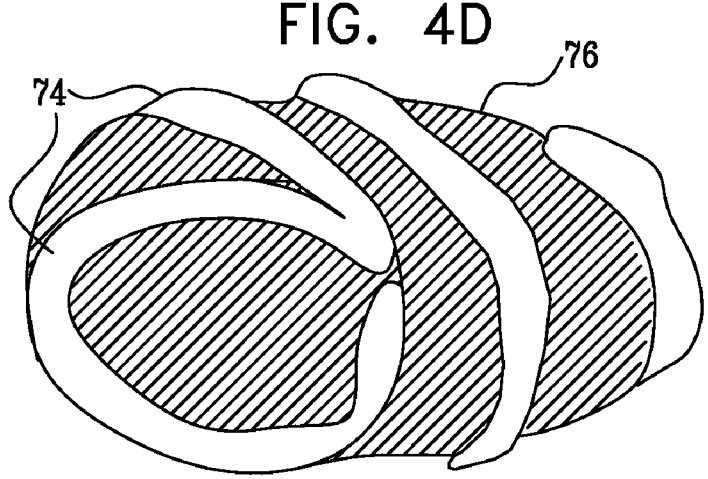
Figure 4E:
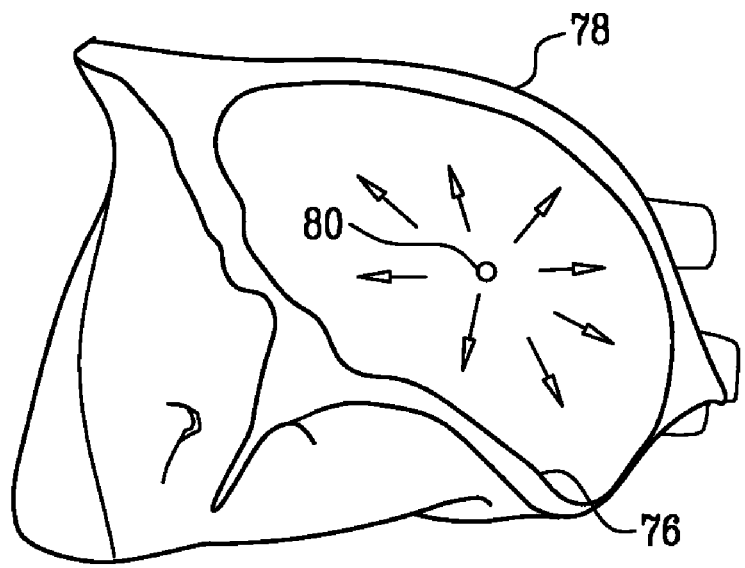

Contour detection and delineation is based on the seed point and is illustrated schematically hereinbelow (FIG. 4E). Detection may include edge detection methods, correlation methods, motion detection methods and other methods known in the art. A well-known method of edge detection is the Canny edge detection method, described in F. J. Canny, "A Computational Approach to Edge Detection," *IEEE Trans PAMI*, 8(6):679-698, 1986. An improved method, based on Canny edge detection, that may be used in this context is described in U.S. Provisional Patent Application 60/915,152, filed May 1, 2007, which is assigned to the assignee of the present patent application and whose disclosure is incorporated herein by reference.

In contrast to segmentation methods such as those described in the abovementioned U.S. Pat. No. 5,903,664 and U.S. Patent Publication 2006/0253024, the seed point determined at step 54 is determined automatically based on the anatomical map. Furthermore, the contour detection performed at step 56 may be based on a seed point that is outside the inner surface of the cavity wall, as that surface appears in the ultrasound image. The points in the anatomical map, and thus the seed point as well, may be located beyond the inner wall due to the pressure that the catheter imposes on the wall during position coordinate acquisition.

The output of step 56 is a matrix in three dimensions defining one or more contours that segment the original ultrasound 3-D image. Alternatively, contours may be defined using parametric equations.

Once a contour is determined according to the above steps, the contour may be applied in subsequent steps of visualizing the ultrasound image and the anatomical map, as described hereinbelow.

At a map enhancement step 60, the resolution of the anatomical map acquired at step 52 is enhanced with points extracted from the contour. As indicated in FIG. 3, step 60 comprises three sub-steps. At a sub-step 62, the contour determined at step 56 is transformed in the 3-D coordinate space to align with the points in the electro-anatomical map, as described further hereinbelow with respect to FIG. 6B. In one embodiment, the transformation of the contour is performed based on a least-squares, best-fit algorithm.

Subsequently, at a point extraction sub-step 64, contour points are extracted from the transformed contour and added to the anatomical map, thereby enhancing the density of the map. Extraction of contour points may be performed automatically by projecting a 2-D grid of a given density onto the surface of the contour and extracting points at grid intersections, as indicated below in FIG. 6C.

Data points used to enhance the anatomical map may also be extracted from 3-D image sources other than the contour derived by the methods described hereinabove. For example, a 3-D anatomical surface registered with the anatomical map, according to the methods of U.S. Patent Publication 2007/0049817 described in the Background, may also provide a source of points that may be added to the anatomical map.

As described above, the anatomical map is generally an electro-anatomical map, though the map may also comprise, alternatively or additionally, other physiological parameters, such as tissue and temperature characteristics. At a sub-step 66, a picture of the enhanced map, including coordinates of the extracted contour points, is displayed. Physiological parameters may be estimated for the added contour points by interpolating and/or extrapolating parameter values from the original map data. The picture is generally displayed as a 3-D image using 3-D visualization methods, including projection of 3-D data onto the 2-D plane of the console display. Typically, the displayed image may be rotated so as to be viewed from multiple perspectives.

At a contour display step 67, the contour determined at step 56 is displayed, using the aforementioned 3-D visualization methods. Physiological parameters from the anatomical map may be interpolated and/or extrapolated over the surface of the contour so as to display the contour with highlighting indicative of the parametric values, as described further hereinbelow with reference to FIG. 7. Highlighting may be indicated by various means, such as coloring or shading.

Similar highlighting of the contour surface may also be used to display image data (i.e., voxels) from the 3-D ultrasound image. Each point of the contour surface may be highlighted according to the value of the voxel at the corresponding coordinates in the 3-D image. The contour may also be highlighted based on 3-D image data extracted from other sources, including Magnetic Resonance Imaging (MRI), Computerized Tomography (CT), or x-ray imaging. The contour may also be transformed by a given radial offset, and the 3-D image data highlighting may be displayed according to the offset coordinates, analogous to viewing onion skins at various depths.

In further embodiments, described hereinbelow with respect to FIGS. 8A and 8B, the image processor may generate a closed volume, rather than a surface, based on the contour. Within the closed volume, voxels extracted from 3-D image sources may be displayed with various degrees of transparency, such that voxels corresponding to unobstructed body cavities appear transparent and voxels corresponding to tissues or other obstructions appear relatively dark and opaque.

At a supplemental acquisition step 68, additional map points are measured with catheter 24 and added to the anatomical map, thereby increasing the map density.

Process 50 may be performed iteratively, in real-time, such that displayed images are updated based on newly acquired data and subsequent calculations based on the newly acquired data.

As described above, the displayed image appears relatively fixed if data acquisition is synchronized to a single timing point in the cardiac cycle. If multiple timing points are chosen, acquisition of the ultrasound image data and the anatomical map data is synchronized to each timing point, and distinct seed points and contours are typically determined for each synchronized set of data. Contour delineation may also be performed by determining a contour at one point in the cardiac cycle, and using the determined contour as part of an automatic process to find the corresponding contour at the next timing point in the cycle.

FIGS. 4-8 are schematic representations of images that visually demonstrate aspects of the modeling methods described above, in accordance with embodiments of the present invention.

FIGS. 4A-4F provide a pictorial view of steps 52-56, whereby a contour is delineated based on a seed point derived from an anatomical map. In FIG. 4A, catheter 24 is inserted into a right atrium 70 of heart 22 and captures 2-D images of the right atrium as well as of a left atrium 72. FIG. 4B shows one of these images (with the intensity scale reversed for visual clarity, so that the interior of the left atrium is light gray, while the more reflective walls of the heart are dark gray). An operator of system 20 delineates an outline 74 of the inner surface of the left atrium as it appears in the image. The operator may trace this outline, for example, by manipulating a cursor 75 on screen using a mouse or other pointing device.

FIGS. 4C and 4D show the user-delineated outlines superimposed on the volume of left atrium 72. Each outline is taken from a different 2-D image, having a location and orientation determined by the location and orientation of catheter 24 when the 2-D image was captured. When sufficient outlines of this sort have been delineated, they define an anatomical map of an inner contour 76 of the left atrium. Alternatively, as noted above, a map of similar shape may be generated by contact mapping, for example by passing the catheter into the left atrium itself and contacting multiple points on the actual inner surface of the left atrium. In this case, the anatomical map may also include electrical data.

Processor 32 places inner contour 76 inside a volume 78 that contains the left atrium, as illustrated in FIG. 4E. Based on the map points on the contour, a seed point 80 is generated, as described at step 54, hereinabove. In one embodiment, the seed point is determined as the center of contour 76 that is generated from the anatomical map points. The surface generated is typically a function fitted to the points on the outlines delineated by the user or mapped by the catheter, using surface generation methods known in the art. As noted above with respect to step 54, the points in the anatomical map may be located beyond the actual inner surface of the wall of the left atrium due to the pressure that the catheter imposes on the wall during position coordinate acquisition.

Processor 32 manipulates contour 76 in three dimensions relative to seed point 80 and the actual edges in the 3-D ultrasound image data that were collected at step 52. In embodiments of the present invention, an edge detection algorithm is implemented to detect a contour corresponding to the inner wall surface. (A method that may be used for this purpose is described, for example, in the above-mentioned U.S. Provisional Patent Application 60/915,152) As illustrated, detection rays are expanded from seed point 80 in the direction of the wall of volume 78. Contour points are detected when the detection rays intersect sets of voxels with intensity variations that match a threshold, according to the Canny edge detection method described above, or other similar algorithms.

Figure 4F:
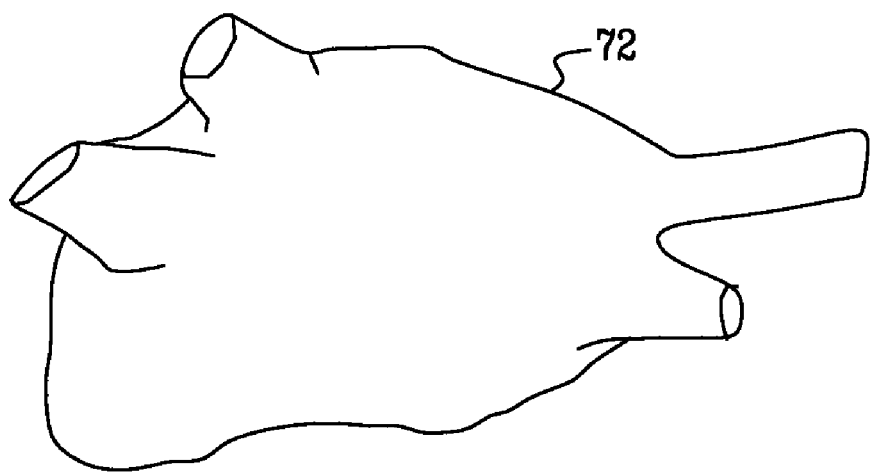

FIG. 4F shows the contour of left atrium 72 that is delineated based on 3-D contour 76. The contour delineation proceeds in three dimensions, thereby generating the contour in the 3-D space of the ultrasound image. As noted earlier, a similar sort of 3-D contour may be generated starting from a 3-D electro-anatomical map, rather than from a map based on user-delineated outlines as shown in this example.

Figure 5A:
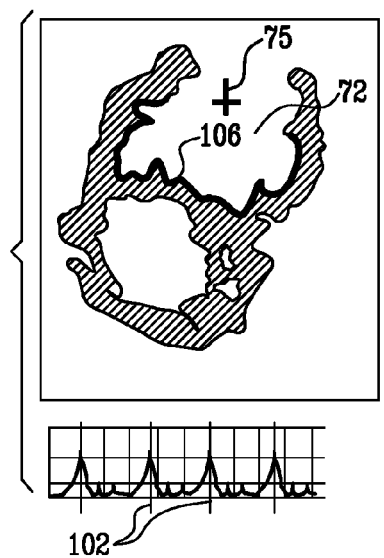
Figure 5B:
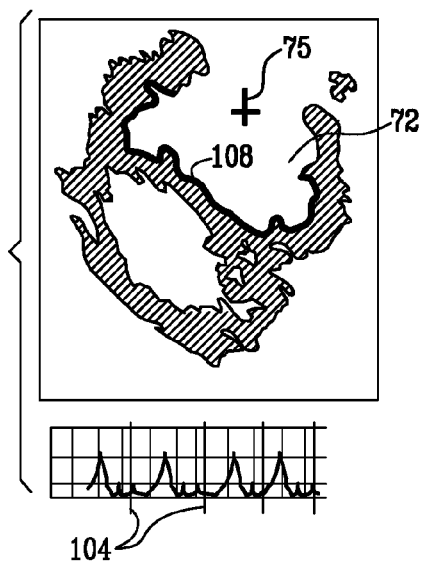

FIGS. 5A and 5B show 2-D slices of the ultrasound image and delineated contour for two distinct timing points in a cardiac cycle. FIG. 5A shows the image when data acquisition was gated at a timing point 102 corresponding with a peak systole of the cardiac cycle; in FIG. 5B the data acquisition was gated at a timing point 104 during the diastole of the cardiac cycle. As described above, anatomical map data is also acquired at each timing point, such that anatomical map data and ultrasound data are synchronized for each timing point. Consequently, distinct contours, respectively contour 106 and contour 108, may be generated for respective timing points 102 and 104.

Figure 6A:
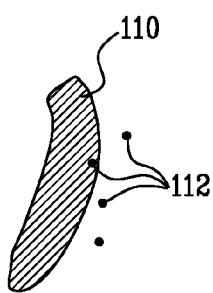
Figure 6B:
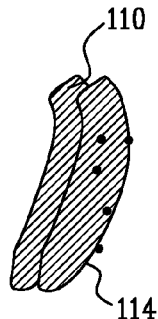
Figure 6C:
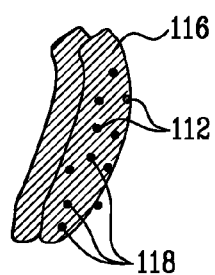

FIGS. 6A-6C provide a pictorial view of map enhancement step 60, described above. FIG. 6A shows a 3-D contour 110 overlaid with map points 112. Contour 110 may be generated as described above with respect to the generation of contour 96, or may be provided by other means known in the art. The map points are comprised in an anatomical map that typically has a low density of points relative to the resolution of the contour.

FIG. 6B shows a contour 114 generated by a transformation of contour 110 to new coordinates, according to sub-step 62, described above.

FIG. 6C provides a visualization of point extraction sub-step 64, described above. Various fixed grid or flexible grid methods may be applied so as to determine points 118 in contour 114 that are to be added to the anatomical map. In one embodiment, a wire-mesh 116 is defined based on contour 114, and mesh intersection points are used to determine points 118. A surface may subsequently be generated from the anatomical map comprising original map points 112 and additional points 118. The surface may be colored or shaded according to physiological parameters comprised in the anatomical map, such as electrical potentials.

Figure 7:
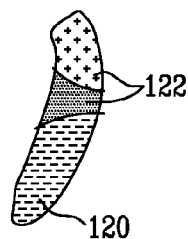

FIG. 7 provides a pictorial view of contour display step 67, described above. Values of physiological parameters from the anatomical map are interpolated and/or extrapolated over a contour surface 120. Whereas highlighting is shown in the figure using text symbols 122, highlighting is typically indicated by other means, such as coloring or shading.

Highlighting may alternatively be based on 3-D image data. Because each point on the contour surface corresponds to a voxel in the 3-D ultrasound image, each contour surface point may be highlighted according to the value of the corresponding voxel. The contour may also be highlighted based on corresponding voxels in 3-D images that are derived from other sources, including MRI, CT, or x-ray imaging, after registering coordinates of these images with the contour using image registration methods known in the art.

In some embodiments, the physician may also specify a contour offset, in order to view voxels from the 3-D image at a given offset from the contour. Specifying an offset generates a transformation of the contour that may be highlighted based on 3-D image data in the manner described above.

Figure 8A:
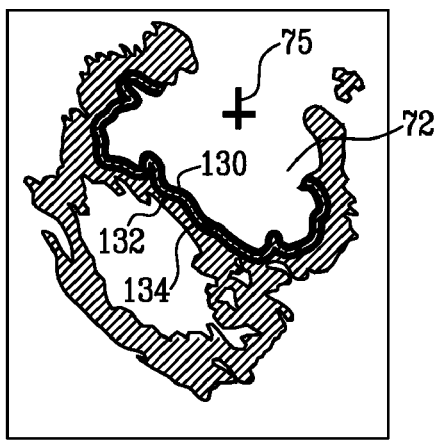
Figure 8B:
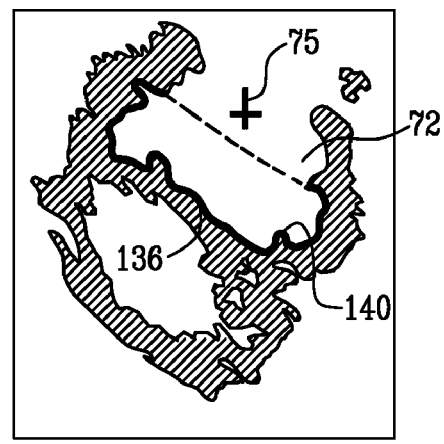

FIGS. 8A and 8B illustrate an additional aspect of contour display step 67, wherein a closed volume bounded by a contour is generated and displayed. Two methods of generating closed volumes are exemplified by FIGS. 8A and 8B, respectively. For the sake of elucidation, the figures represent contours in two dimensions, based on the representation shown in FIG. 4D.

FIG. 8A illustrates generation of a closed volume based on transforming a first contour 130 to generate a second contour 132, such that the closed volume is bounded by the two contours. In one embodiment, the transformation is implemented such that each point on the first contour is transformed by a set distance in a radial direction defined by the location of the catheter indicator. A closed volume 134 is defined between the two contours, thereby providing in effect a contour with a given thickness.

FIG. 8B illustrates an alternative method of generating a closed volume 138, whereby the closed volume is defined as the space bounded at least on one side by the convex surface of the contour. If the contour itself is not a closed surface, but rather has an open edge, as shown in the figure, then a surface connecting points of the open edge may be generated, thereby closing the volume.

Within a generated closed volume, voxels extracted from a 3-D image source, such as the 3-D ultrasound image, may be displayed with various degrees of transparency. Voxels corresponding to unobstructed body cavities are displayed as being transparent and voxels corresponding to tissues or other obstructions, such as an obstruction 140, are displayed relatively dark and opaque.

Although the embodiments described above relate specifically to ultrasound imaging using an invasive probe, such as a cardiac catheter, the principles of the present invention may also be applied in reconstructing 3-D models of organs using other external or internal ultrasound probes (such as a transthoracic probe), fitted with a positioning sensor. Additionally or alternatively, as noted above, the disclosed method may be used for 3-D modeling of organs other than the heart and using 3-D images derived from imaging methods other than ultrasound, including MRI, CT, and x-ray imaging. Further additionally or alternatively, as described above, other diagnostic or treatment information, such as tissue thickness and temperature, may be overlaid on the 3-D model in the manner of the electrical activity overlay. The 3-D model may also be used in conjunction with other diagnostic or surgical tools, such as ablation catheters, as well as in conjunction with other procedures, such as an atrial septal defect closing procedure, spine surgery, and particularly minimally-invasive procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method of medical imaging, comprising:
generating fields with field generating coils defining a coordinate space;
creating an anatomical map of an inner wall of a cavity in a body of a subject by inserting a probe into the body and collecting data using the probe in the coordinate space;
creating a three dimensional (3-D) ultrasound image of the cavity, wherein creating the 3-D ultrasound image comprises determining first coordinates of pixels of the 3-D ultrasound image in the coordinate space, and bringing the probe into contact with the inner wall of the cavity and measuring second coordinates in the coordinate space of one or more locations on the inner wall and wherein the anatomical map is created using a first probe, and wherein the 3-D ultrasound image is captured using a second probe comprising an ultrasonic transducer, wherein the first probe and the second probe comprise respective first and second position sensors, and wherein the method comprises using the position sensors to sense the generated fields from the field generating coils and calculating positions of the first probe and the second probe responsively to the sensed fields; and
delineating a 3-D contour in the 3-D image based on the map.

2. The method of claim 1, wherein delineating the contour comprises determining a seed point based on the anatomical map.

3. The method of claim 2, wherein delineating the contour comprises identifying a point on the contour located between the seed point and the cavity.

4. The method of claim 1, wherein creating the anatomical map comprises inserting the probe into the cavity and bringing the probe into contact with the inner location at multiple locations.

5. The method of claim 4, wherein the anatomical map comprises a plurality of first points, each associated with a respective measurement of a physiological parameter made by the probe in contact with the inner wall, and wherein the method comprises adding to the anatomical map a plurality of second points based on the contour, and generating a display of the anatomical map showing a distribution of the physiological parameter over the first and second points.

6. The method of claim 5, wherein the physiological parameter is selected from a group of parameters consisting of cardiac electrical activity, a tissue characteristic, a temperature, and a blood flow.

7. The method of claim 1, wherein creating the 3-D ultrasound image comprises capturing multiple two-dimensional (2-D) ultrasound images using an ultrasonic transducer in the probe, and combining the 2-D ultrasound images to generate the 3-D image.

8. The method of claim 7, wherein creating the anatomical map comprises delineating respective 2-D contours in a plurality of the 2-D ultrasound images, and combining the 2-D contours to produce the anatomical map.

9. The method of claim 1, wherein the probe comprises an ultrasonic transducer and a position sensor, and is used both to create the anatomical map and to capture the 3-D ultrasound image.

10. The method of claim 1, and comprising synchronizing a timing of capturing the ultrasound image and creating the anatomical map relative to a synchronizing signal selected from a group of signals consisting of an electrocardiogram (ECG) signal, an internally-generated synchronization signal and an externally-supplied synchronization signal.

11. The method of claim 10, wherein the timing is synchronized to multiple timing points in a cardiac cycle, and the method comprises generating a display of one or more of the anatomical map, the ultrasound image, and the contour as a moving image.

12. The method of claim 1, wherein capturing the 3-D image comprises scanning the anatomical structure using an extracorporeal ultrasound probe.

13. The method of claim 1, and comprising generating a display of the contour showing a distribution over the contour of data from at least one imaging modality selected from a group of modalities consisting of ultrasound imaging, Magnetic Resonance Imaging (MRI), Computerized Tomography (CT), and x-ray imaging.

14. The method of claim 1, and comprising identifying a volume bounded by the contour and generating a display showing a distribution within the volume of voxels from a 3-D imaging modality.

15. The method of claim 1, wherein the cavity is a chamber of a heart.

16. A system for medical imaging, comprising:
field generating coils for generating fields and defining a coordinate space;
at least one probe comprising a first position sensor, which is configured to be inserted into a cavity in a body of a subject in the coordinate space and to collect data for use in creating an anatomical map of an inner wall of the cavity and a second probe comprising a second position sensor for capturing a three-dimensional (3-D) image in the coordinate space, the first position sensor of the at least one probe and the second position sensor of the second probe sensing generated fields from the field generating coils; and a processor, which is configured to calculate positions of the at least one probe and the second probe respectively based on the generated fields using the first position sensor and the second position sensor respectively and to generate the 3-D image of the cavity from the second probe and to delineate a 3-D contour in the 3-D image based on the map.

17. The system of claim 16, wherein the anatomical map comprises a plurality of first points, each associated with a physiological parameter measured by bringing the probe into contact with the inner wall, wherein the processor is further configured to add to the anatomical map a plurality of second points based on the contour and to generate a picture of the anatomical map showing a distribution of the physiological parameter over the first and second points, wherein the system comprises a display configured to show the picture.

18. The system of claim 16, and comprising:
one or more radiators, coupled to generate fields in a vicinity of the at least one probes; and
at least one position sensor, which is associated with the at least one probe and is coupled to transmit signals responsively to the generated fields, wherein the processor is configured to determine coordinates of the at least one probe responsively to the signals.

19. The system of claim 18, wherein the processor is coupled to calculate first coordinates of the at least one position sensor in a given three-dimensional coordinate space responsively to the sensed fields and to determine, based on the first coordinates and second coordinates of pixels of the 3-D image in the given three-dimensional coordinate space, and to determine third coordinates in the given three-dimensional coordinate space of one or more locations on the inner wall.

20. The system of claim 16, wherein the cavity comprises a chamber of a heart, and wherein the at least one probe comprises at least one catheter, which is inserted into the chamber so as to acquire the 3-D image and the coordinates of the anatomical map.

21. The system of claim 16, wherein the at least one probe comprises an ultrasonic transducer and a position sensor, and is used both to create the anatomical map and to capture the 3-D image.

22. The system of claim 16, wherein the at least one probe and the processor are coupled to synchronize a timing of acquisition of the 3-D image and the coordinates of the anatomical map relative to a synchronizing signal selected from a group of signals consisting of an electrocardiogram (ECG) signal, an internally-generated synchronization signal and an externally-supplied synchronization signal.

23. The system of claim 22, wherein the timing is synchronized to multiple timing points in a cardiac cycle, and wherein the processor is configured to generate a display of one or more of the anatomical map, the ultrasound image, and the contour as a moving image.

24. The system of claim 16, wherein the processor is configured to generate a display of the contour showing a distribution over the contour of data from at least one imaging modality selected from a group of modalities consisting of ultrasound imaging, Magnetic Resonance Imaging (MRI), Computerized Tomography (CT), and x-ray imaging.

25. The system of claim 16, wherein the processor is configured to identify a volume bounded by the contour and to generate a display showing a distribution within the volume of voxels from a 3-D imaging modality.

26. A computer software product for medical imaging, the product comprising a non-transitory computer-readable medium in which program instructions are stored, which instructions, when read by a computer, cause the computer to acquire a three-dimensional (3-D) image of a cavity in a body of a subject with a first probe, and to determine coordinates of an anatomical map of an inner wall of the cavity with a second probe, and to delineate a 3-D contour in the 3-D image based on the map.

* * * * *